United States Patent [19]
Andersch et al.

[11] Patent Number: 5,804,208
[45] Date of Patent: Sep. 8, 1998

[54] GRANULATES CONTAINING MICRO-ORGANISMS

[75] Inventors: Wolfram Andersch, Bergisch Gladbach; Rüdiger Hain, Langenfeld; Michael Kilian, Köln, all of Germany

[73] Assignee: Bayer Aktiengesellschaft, Leverkusen, Germany

[21] Appl. No.: 836,883

[22] PCT Filed: Nov. 15, 1995

[86] PCT No.: PCT/EP95/04491

§ 371 Date: May 20, 1997

§ 102(e) Date: May 20, 1997

[87] PCT Pub. No.: WO96/16547

PCT Pub. Date: Jun. 6, 1996

[30] Foreign Application Priority Data

Nov. 28, 1994 [DE] Germany .................. 44 42 255.5

[51] Int. Cl.[6] .................. A01N 25/26; A01N 63/00
[52] U.S. Cl. .................. 424/407; 424/405; 424/406; 424/410; 424/418; 424/93.5; 504/117; 435/254.1

[58] Field of Search .................. 424/405, 406, 424/407, 410, 418–420, 93.1, 93.2, 93.3, 93.5; 504/117; 435/254.1

[56] References Cited

U.S. PATENT DOCUMENTS

| | | | |
|---|---|---|---|
| 5,074,902 | 12/1991 | Connick, Jr. et al. | 71/79 |
| 5,418,164 | 5/1995 | Andersch et al. | 435/254.1 |
| 5,589,390 | 12/1996 | Higuchi et al. | 435/307.1 |

FOREIGN PATENT DOCUMENTS 298038 2/1992 Germany .

*Primary Examiner*—Neil S. Levy
*Attorney, Agent, or Firm*—Sprung Kramer Schaefer & Briscoe

[57] ABSTRACT

The present invention relates to novel pesticides consisting of granules in which the carrier material is semolina and in which the surface of this carrier material carries microorganisms suitable for controlling pests, their preparation and use for controlling pests.

9 Claims, No Drawings

GRANULATES CONTAINING MICRO-ORGANISMS

The present invention relates to novel pesticides consisting of granules in which the carrier material is semolina and in which the surface of this carrier material carries microorganisms suitable for controlling pests, their preparation and use for controlling pests.

It has already been disclosed that certain microorganisms (bacteria, fungi and viruses) can be pathogenic to pests, such as insects, nematodes or phytopathogenic fungi, and thus be employed in controlling pests. In many cases, however, great difficulties are encountered in making available suitable microorganism preparations (formulations) having a standardized activity and commercial applicability because the formulation of the microorganisms is complicated and often adversely affects their activity and storage stability.

This invention now provides novel pesticides consisting of granules comprising microorganisms, characterized in that the carrier material of the granules is semolina and the microorganisms suitable for controlling pests are located on the surface of this carrier material.

Pesticides are all compositions according to the invention suitable for controlling undesirable animal and plant pests and nuisance pests (such as harmful arthropods and nematodes, broad-leaved weeds and grass weeds, harmful bacteria and fungi). In general, the activity of these pesticides is based on the antagonistic action (parasitization, toxin formation, competition behaviour) of the micoorganisms used against the pests, resulting in their containment or destruction. The pesticides are preferably employed in the areas of agriculture, forestry, horticulture, household and hygiene, protection of stored products and materials, in particular for the protection of plants or harvested products. Preferred pesticides according to the invention are those suitable for controlling pests encountered in the soil region.

Preferred compositions according to the invention are the pesticides, preferably for controlling animal pests (preferably arthropods and nematodes, in particular insects and nematodes, very particularly preferably insects) and of microbial pests (such as harmful bacteria and fungi), in particular, however, of animal pests.

Microorganisms which can be used according to the invention are all microorganisms (bacteria and fungi) capable of forming resting forms, such as spores or conidia.

The microorganisms have to be able to affect the vitality or reproductive capacity of the pests to be controlled in such a way that they can be sufficiently controlled by the action of the pesticides. For this purpose, the microorganisms which can be used according to the invention have to be capable of releasing substances into the surroundings which have a corresponding action on the pests or else are capable of parasitizing the pests sufficiently.

The microorganisms used according to the invention should not exhibit any pathogenic properties with regard to warm-blooded animals and, in addition, should not damage beneficial animals (e.g. earthworms, bees) to a considerable extent.

The formation of resting forms, in particular blastospores, spores and conidia, can be effected by a multitude of microorganisms (bacteria, fuingi), preferably by fuingi from the taxonomic classes of the Phycomycetes, Ascomycetes, for example Chaetomium, Basidiomycetes and Deuteromycetes, in particular by the representatives of the Fungi imperfecti, such as, for example, various species of Aspergillus, Altemnaria, Aphanocladium, Beauveria, Coniothyrium, Colletotrichum, Meria (Drechmeria), Penicillium, Fusarium, Gliocladium, Pseudocercosporella, Trichoderma, Verticillium, Paecilamyces, in particular also of Metarhizium and Gliocladium, especially preferably of Metarhizium. Numerous strains of these fungi exhibit an antagonistic activity towards soil-borne, phytopathogenic fungi, such as, for example, *Trichoderma hamatum* and *Glioclacium roseum, Gliocladium virens* or apathogenic strains of otherwise phytophathogenic strains, such as, for example, apathogenic Fusarium oxysporum strains, against weeds, such as, for example, *Alternatia cassiae, Fusarium lateritum, Fusarium solani,* or against harmful insects, such as, for example, *Verticillium lecanii, Aspergillus parasiticus,* and in particular *Metarhizium anisopliae*. Examples of bacteria which can be used according to the invention are *Bacillus thuringiensis* and *Bacillus subtilis*.

Preferred microorganisms are fungicidal, nematopathogenic and entomophathogenic microorganisms (in particular fungi from the class Deuteromycetes). Especially preferred are nematophatogenic and entomophatogenic microorganisms.

Very particularly preferred are fungi of the genus Metarhizium, in particular the species *Metarhizium anisopliae* and especially the *Metarhizium anisoliae* strains P 0001 and P 0003, in particular the strain P 0001. These strains, which can be particularly advantageously used according to the invention, have been disclosed in EP-A-0 268 177. They were deposited on 24.10.1986 with the Deutsche Sammlung von Mikroorganismen (DSM), Grisebachstraβe, D-3400 Göttingen, Bundesrepublik Deutschlang in accordance with the terms of the Budapest Treaty on the International Recognition of the Deposit of Microorganisms for the Purposes of Patent Procedure, and have the accession numbers:

DMS 3884 (P 0001) and
DMS 3885 (P 0003).

The present invention also relates to the use of the mutants and variants of these strains which have the characteristics and properties essential for carrying out the invention. According to the process according to the invention, these Metarhizium strains afford granules having very advantageous biological properties, which allow the use of these granules as pesticides, preferably for controlling arthropods and nematodes, in particular insects and nematodes (especially insects) and very particularly preferably soil insects, that is insects encountered in the soil, on the ground or in plant material near the ground.

In the granules according to the invention, the microorganisms can be present in various forms and development stages (for example in the form of mycelia, spores, blastospores etc.). Preferably, they are present as resting forms, in particular in the form of spores or conidia.

The carrier material of the microorganism-containing granules according to the invention is semolina.

Semolina is to be understood as meaning cereal particles of irregular shape, preferably without glumes, as are formed when crushing cereals. Suitable cereals are the customary cereal varieties, such as wheat, oats, rye, maize, millet and rice. According to the invention, preference is given to using wheat semolina, durum wheat semolina is especially preferred. Owing to the crushing process, the semolina particles are of irregular shape. Owing to the particularly advantageous handling properties, preference is given to semolina which particles are as close as possible to a globular shape. Commercial semolina is preferably used. The semolina to be used according to the invention consists of particles which preferably have a mean diameter of 0.05 to 3, especially preferably of 0.1 to 2.5 and very especially preferably of 0.15 to 2.0 mm. These dimensions stated also apply to the ready-to-use pesticide.

In the granules according to the invention, the microorganisms are located on the surface of the carrier material, that is the semolina particles. This means that the microorganisms adhere to the surface of the carrier material with the aid of suitable adhesives, the adhesive properties depending on the kind of adhesive used in each case.

In a particular embodiment of the invention, the granules according to the invention consist of the semolina carrier material and a material coating this carrier material which comprises an adhesive, the microorganisms, preferably in the form of resting forms (in particular spores or conidia) and optionally further auxiliaries and optionally active compounds suitable as pesticides.

In a further preferred embodiment of the invention, the granules contain (on the surface of the semolina particles) $2\times10^3$ to $2\times10^{10}$, especially preferably $2\times10^5$ to $2\times10^8$ microorganism particles (preferably spores or conidia) per gram of granules.

Suitable adhesives with the aid of which the microorganisms (in particular their spores or conidia) adhere to the surface of the semolina particles, i.e. which link them to the semolina particles, are the common natural or artificial adhesives which are non-toxic towards the microorganisms. For example, adhesives customary in the mid-life range can be used. Examples are adhesives based on cellulose (for example methylcellulose), based on starch, dextrans, alginates, agar-agar, gelatin, gum arabic, tragacanth, casein sizes, gluten sizes, polyvinyl alcohols and polyvinyl acetates and the mixtures of these materials.

Methylcellulose is particularly preferably used.

The coating of the granules according to the invention can, in addition to the adhesives and the microorganisms, comprise further auxiliaries, which self-evidently have to be non-toxic for the microorganisms. Suitable auxiliaries are for example those customary in the field of food technology. Such auxiliaries include for example antioxidants protecting the microorganisms from oxidation reactions, such as ascorbic acid, 2,3-tert-butyl-4-hydroxy-anisole etc. or substances which protect the microorganisms from drying out too much, such as polyalcohols, (for example glycerol), sugar, lipids etc.

Suitable auxiliaries are, for example, also colorants, which facilitate the determination of the density of the microorganisms on the carrier material or mark the respective product. Suitable auxiliaries are optionally also nutrients (carbon and nitrogen sources) which facilitate or accelerate growth of the microorganisms after the application of the pesticides according to the invention. This may be, for example, the nutrient media which are also used for growing the respective microorganisms.

The adhesives and auxiliaries which are particularly suitable in each case can easily be identified by a person skilled in the art with the aid of simple routine experiments. With respect to the necessity of an economical preparation of the pesticides according to the invention, the easy availability of the adhesives and the auxiliaries in each case plays an important role in their selection.

In addition, the coating of the granules according to the invention may also contain pesticidally active chemicals which can enhance the activity of the microorganisms or widen the spectrum of activity of the pesticides. Synergistic actions between the microorganisms and the active chemicals are also possible. Suitable chemicals are those active compounds which are non-toxic to the respective microorganisms and, preferably, have the same direction of activity. Thus, for example, entomopathgenic microorganisms can be combined with insecticidal compounds. With the aid of simple routine experiments, a person skilled in the art can easily determine which of the active compounds are non-toxic to the microorganisms employed in each case and may thus be additionally present on the granules.

Insecticidal compounds which can be present in the coating of the granules are, for example, phosphoric esters (for example phostebupirim), pyrethroids (for example cyfluthrin and β-cyfluthrin), nicotinyl insecticides (for example imidacloprid) or carbamates (for example carbofuran). Correspondingly, the granules may also contain synthetic fungicides or herbicides.

In a very particularly preferred embodiment of the present invention, the pesticides according to the invention comprise durum wheat semolina as carrier material which is coated by a material consisting essentially of an adhesive based on cellulose, preferably methylcellulose, and conidia of fungi of the genus Metarhizium, in particular of the species Metarhizium anisopliae and very particularly preferably of the Metarhizium anisopliae strains P 0001 and/or P 0003. These granules can be used particularly advantageously for controlling insects, in particular soil-dwelling insects.

The novel pesticides are simple and economically particularly advantageous to prepare. In addition, they exhibit a surprisingly high activity, measured by the amount of the microorganisms employed. Furthermore, the novel compositions are notable for high storage stability and very simple handling (for example transferability, free flow, meterability and ease of application). Since the microorganisms are firmly attached to the surface of the carrier materials, there is hardly a any dust formation during the handling of the compositions, which can be of considerable practical importance in particular in biological pesticides, not least because of hygiene reasons (in particular in the case of allergic persons).

The present invention also provides a process for preparing the pesticides according to the invention, characterized in that the respective microorganisms (in the form of mycelium particles, spores or conidia) are suspended in a customary manner in an aqueous solution containing the adhesive and optionally auxiliaries and optionally pesticidally active compounds, the suspension is mixed with the semolina, the granules are separated off and dried.

It is also possible to carry out the individual process steps, which are carried out according to customary procedures and methods (such as those used in microbiology, food technology and the technology of crop protection agents), in a different sequence. For example, a suspension of the microorganisms can be initially prepared and the adhesive (optionally as an aqueous solution or suspension) is then added. It is also possible to apply auxiliaries or active compounds to the granules in more than one step, i.e., for example, to glue the microorganisms in a first step onto the carrier and to add auxiliaries or active compounds in a second step. It is also possible to use a customary fluidized-bed process to glue the microorganisms onto the carrier.

The microorganisms to be used according to the invention can be obtained by conventional fermentation processes. The fermentation can be carried out using solid, semi-solid or liquid nutrient media. If spores or conidia are used, preference is given to solid or semi-solid nutrient media. Preference is given to semi-solid nutrient media in surface culture, in which case the fermentation is carried out for example in dishes or in plastic bags or sacks. The nutrient media contain the nutrients suitable and known for the cultivation of the respective microorganisms, in particular one or more metabolizable carbon sources or nitrogen sources and mineral salts. These products may be present in the form of the individual components, but also in the form of complex mixtures as represented in particular by biological products of various origin. Suitable carbon sources are all customary carbon sources. Examples include carbohydrates, in particular polysaccharides, such as starch or dextrins, disaccharides, such as maltose or sucrose, monosaccharides, such as glycose or xylose, sugar alcohols, such as mannitol or glycerol, and also naturally occurring mixtures, such as malt extract, molasses or whey powder. Suitable nitrogen sources are all customary organic and inorganic nitrogen sources. Examples include proteins, protein hydrolysates, amino acids, such as glutamic acid, aspartic acid, arginine, lysine, ornithine or serine, nucleoside bases, such as cytosine or uracil, as well as soya bean flour, cottonseed flour, lentil flour, pea flour, soluble and insoluble vegetable proteins, corn steep liquor, yeast extract, peptones and meat extract, and also ammonium salts and nitrates, for example $NH_4Cl$, $(NH_4)_2SO_4$, $NaNO_3$ and $KNO_3$. The mineral salts which the nutrient medium should contain yield for example the following ions:
$Mg^{++}$, $Na^+$, $K^+$, $Ca^{++}$, $NH_4^+$, $Cl^-$, $SO_4^{--}$, $PO_4^{---}$ and $NO_3^-$ as well as ions of the customary trace elements, such as Cu, Fe, Mn, Mo, Zn, Co, and Ni. If the carbon sources or nitrogen sources, or the water used, do not contain a sufficiently great amount of these salts or trace elements, it is expedient to supplement the nutrient medium accordingly.

The fermentation is carried out at temperatures between about 15° and about 40° C., preferably between 20° and 35° C.

As already mentioned, the generation of spores or conidia (for example of Metarhizium, Beauveria or Gliocladium) can be carried out in a particularly advantageous manner using solid or semi-solid nutrient media in surface culture. To obtain the conidia or spores, they can simply be shaken off or rinsed off with water. To facilitate removal by rinsing off, a (preferably non-ionic) emulsifier can be added.

In a preferred embodiment of the novel process for preparing the granules, the spores or conidia are initially suspended in water, in which case it can be advantageous to employ a non-ionic emulsifier or another suitable dispersant for better distribution of the spores or conidia. The suspension is then added to an aqueous solution of the adhesive (which optionally contains further auxiliaries and/or active compounds) while stirring or shaking. The microorganism suspension obtained in this manner is subsequently carefully mixed with the semolina serving as carrier. The microorganism suspension can also be sprayed onto the carrier material, for example in a fluidized-bed dryer.

If, instead of spores or conidia, mycelium particles are to be used, the mycelium is separated off in a customary manner from the fermentation broth and, optionally after drying, broken up. The mycelium particles are then applied to the carrier material in a manner analogous to the above-described procedure for spores or conidia.

To avoid contamination of the cell granules by undesired microorganisms which might cause deterioration of the quality or destruction of the product by their metabolic activities, all the process steps of the granule preparation (and, if appropriate, further work-up) are advantageously carried out under sterile conditions.

To dry the granules, the customary methods for drying biological material by means of heat transfer by convection, such as, for example, the processes of spray drying, flow drying and fluidized-bed drying, or by means of heat transfer by contact, such as, for example, the processes of plate drying, pedal drying, tumble drying, conveyor drying, drum drying, vacuum chamber drying and lyophilization in vacuo can be employed. The drying process can also consist of a combination of two or more of these processes. The dehydration of the granules is carried out batchwise or continuously, preferably however batchwise. The processes in detail are to be designed in such a way that the viability of the microorganisms on the granules is ensured over as long a period as possible. Furthermore, when drying the granules care has to be taken to keep the mechanical stress to the granules as low as possible.

As already mentioned, it may be advantageous to treat the granules prior to drying with appropriate protective substances, to protect the microorganisms on the granules from damage that may occur during the drying process owing to a fall or rise in temperature or by a too intensive dehydration. Suitable for this are organic or inorganic substances known for this purpose, which, in a defined form or as complex mixture, can achieve a protective action, for example polyalcohols, such as sugar or glycerol. The treatment is carried out using the customary methods by dipping, washing, spraying or mixing the granules with the protective agents.

Protection of the microorganisms on the granules from uncontrolled oxidation reactions can be achieved by treating the granules prior to drying with non- toxic antioxidants, such as, for example, ascorbic acid, 2,3-tert-butyl-4-hydroxy-anisole, 2,6-di-tert-butyl-p-cresol, porpyl gallates or nordihydroguaiaretic acid. The treatment is carried out with the aid of the customary methods by dipping, washing, spraying or mixing the granules with the protective agents.

To develop a rapid biological activity in pest control, the granules can also be treated prior to drying with materials supporting the rehydration of the microorganisms. Suitable for this purpose are all non-toxic hygroscopic materials, in particular polyalcohols such as glycerol, sugar, sugar polymers or derivatives of the sugar polymers.

To activate and intensify the biological action in particular in controlling pests, it can also be advantageous to treat the granules prior to drying with nutrients supporting a rapid multiplication of the microorganisms and thus more dense population of the site of action.

Suitable nutrient-like substances are all metabolizable carbon sources and nitrogen sources which can also be used for growing or during the fermentation of the respective microorganism.

The granules according to the invention are stored in closed containers under dry conditions, preferably at temperatures between 0° C. and 25° C. To maintain the viability of the microorganisms in the granules it may be advantageous to store the granules with the exclusion of oxygen, which can be achieved for example by storage under an atmosphere of nitrogen, carbon dioxide or other inert gases, or of gas mixtures of the gases mentioned, furthermore, the exclusion of oxygen can be achieved by packing the granules under conditions of reduced pressure. If appropriate, it can also be advantageous to add drying agents, for example silica gel, to the packing to enhance the viability of the microorganisms.

The active compounds according to the invention, when using the appropriate microorganisms, are suitable for controlling animal pests, preferably arthropods and nematodes, in particular insects and arachnids, which are encountered in agriculture, in forestry, in horticulture, in the protection of stored products and of materials, and in the hygiene field.

They are active against normally sensitive and resistant species and against all or individual stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec..*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Malanoplus differentialis* and *Schistocerca gregaria.*

From the order of the Dermaptera, for example, *Forficula auricularia.*

From the order of the Isoptera, for example, *Reticulitermes spp..*

From the order of the Anoplura, for example, *Phylloxera vastatrix, Pemphigus spp., Pediculus humanus corporis, Haematopinus spp.* and *Linognathus spp..*

From the order of the Mallophaga, for example, *Trichodectes spp.* and *Damalinea spp..*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp..*

From the order of the Homoptera, for example, *Aleurodes brassicae, Bemisia tabaci, Trialeurodes vaporariorum, Aphis gossypii, Brevicaryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Naphotettix cincticeps, Lecanium corni, Saissetia oleae, Laodelphax striatellus, Nilaparvata lugens, Aonidiella aurantii, Aspidiotus hederae, Pseudococcus spp.* and *Psylla spp..*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofirnannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochlearia, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp..*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, Xenopsylla cheopis and *Ceratophyllus spp.*

From the order of the Arachnida, for example, *Scorpio maurus* and *Latrodectus mactans.*

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The phytoparasitic nematodes include *Pratylenchus spp., Radopholus similis, Ditylenchus dipsaci, Tylenchulus semioenetrans, Heterodera spp., Globodera spp., Meloidogyne spp., Aphelenchoides spp., Longidorus spp., xiphinema spp.* and *Trichodorus spp.*

Preference is given to using the novel pesticides for controlling insects and nematodes, preferably insects, encountered in the soil or on the ground (or near to the ground) (soil-dwelling insects).

The pesticides can also be employed in traps, if appropriate after adding baits or attractants.

The pesticides according to the invention, when using the appropriate microorganisms, can be used for controlling harmful microbes (fungi and bacteria).

Fungicidal compositions in crop protection are employed for controlling Plasmodiophoromycetes, Oomycetes, Chytridiomycetes, Zygomycetes, Ascomycetes, Basidiomycetes and Deuteromycetes.

Bactericidal compositions in crop protection are employed for controlling Pseudomonadaceae, Rhizobiaceae, Enterobacteriaceae, Corynebaceteriaceae and Stroptomycetaceae.

By way of example but not by way of limitation, some causative organisms of fungal and bacterial diseases belonging to the above listed generic terms shall be mentioned:

Pseudomonas species, such as, for example, *Pseudomonas solanacearum;* Pythium species, such as, for example, *Pythium Ultimum;*

Phytophthora species, such as, for example, *Phytophthora cactorum;*

Fusarium species, such as, for example, *Fusarium oxysporum;*

Botrytis species, such as, for example, *Botrytis cinerea*

Pseudocercosporella species, such as, for example, *Pseudocercosporella herpotrichoides;*

Rhizoctonia species, such as, for example, *Rhizoctonia solani;*

Scierotium species, such as, for example, *Sclerotium rolfsii;*

Sclerotinia species, such as, for example, *Sclerotinia sclerotiorum;*

Verticillium species, such as, for example, *Verticillium alboatrum;*

Phialophora species, such as, for example, *Phialophora cinerescens*;

Phomopsis species, such as, for example, *Phomopsis sclerotioides*.

The pesticides according to the invention, when using suitable microorganisms, can furthermore be used as defoliants, desiccants, agents for destroying broad-leaved plants and, especially, as weed-killers. By weeds, in the broadest sense, there are to be understood all plants which grow in locations where they are undesired. The selectivity of the herbicides depends essentially on the particular amount used.

The compositions according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for weed control for example on industrial terrain and on rail tracks, and on paths and areas with or without tree stands. Equally the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, and for selective weed control in annual crops.

The compositions according to the invention can also be used as a mixture with other known pesticides such as insecticides, acaricides, nematicides, protective agents against ingestion by birds, plant nutrients, herbicides and soil structure enhancers.

The application of the compositions according to the invention is carried out in a customary manner, preferably by spreading or incorporation into the soil. Particular preference is given to applying the compositions according to the invention without further formulation, the application being preferably carried out by incorporation into the soil.

The amount of the composition applied can vary within a substantial range. It depends essentially on the nature of the desired effect and the kind of microorganisms employed. In general, the application rates in the areas of agriculture, forestry and horticulture are between 0.1 and 50 kg of composition per hectare of soil, preferably between 1 and 25 kg per ha.

The pesticides according to the invention preferably serve for soil treatment. This way, preferably pests, in particular insects encountered on the ground are controlled.

The present invention is to be illustrated by the following examples. If not stated otherwise, all percentages are per cent by weight.

Example A (Preparation of granules)

1. Growing of conidia

Oatmeal agar (composition: 30 g of oat flakes and 20 g of agar) in a Petri dish is inoculated with 3 week old conidia of the *Metarhizium anisopliae* strain P 0001 (DSM 3884). To multiply the conidia, the dish is kept at 22° to 25° C. in the incubator for 5 days.

2. Preparation of a conidia suspension.

The conidia formed are transferred from the agar of the Petri dish (see above) into a 300 ml Erlenmeyer flask by shaking, and stirred with 50 ml of water containing 1% (per cent by weight) of a non-ionic emulsifier based on polyoxyethylene (20) sorbitan monolaurate (Tween® 20, trademark of ICI America, Inc.) for about 1–2 hours at 700 rpm until a suspension is obtained in which the conidia are present as isolated particles.

The conidia titre is determined using a Neubauer chamber. In the present case it was $5 \times 10^9$ conidia/ml.

3. Preparation of the conidia suspension to be applied to the carrier material.

1 g of methylcellulose (Mowiol® 3–83) are dissolved in 45 ml of water at max. 50° C. 1 g of Ponceau 4RC70 may be added to this solution. The addition of this red dye is optional and immaterial to the preparation process and may thus also be omitted without any adverse consequences.

After cooling, 5 ml of the conidia suspension obtained according to 2. above are added to the solution obtained in this manner and stirred well.

4. Preparation of the granules.

5 ml of the suspension obtained according to 3. above are rapidly stirred with 50 g of durum wheat semolina in a 250 ml beaker until the semolina has absorbed most of the liquid and a homogeneous distribution has occurred (this can particularly easily be monitored with the aid of the optionally added dye).

Using a sieve, the granules formed are separated off from the liquid and dried at 25° C. in a drying cabinet.

The granules obtained can be kept for example under reduced pressure in aluminium bags, for example at a temperature of 4° C.

The product obtained in this manner has the following composition (% is % by weight):

$5 \times 10^7$ conidia per g of granules 0.2% of methylcellulose optionally: 0.2% of Ponceau 3–83

0.01% of emulsifier (Tween® 20)

remainder to 100%: durum wheat semolina

The durum wheat semolina used in the examples has the following properties:

It contains:

69% carbohydrates

12% proteins 4.5% total fibres 0.7% minerals remainder: water and unidentified substances.

1 g of durum wheat semolina consists of about 14,000 particles.

One particle carries about 3,500 konidea.

Example B (Bioloical activity)

Example B1

Test insect: Otiorhynchus sulcatus 1.2–1.3 (vine weevil)

Test granules: granules with Metarhizium anisopliae (obtainable according to Example A)

Experiment:

The granules are mixed under the test soil using customary mixers. The test soil consists of a customary peat-containing soil substrate. The concentration of the granules in the soil is stated in ppm (mg/l, w/v-%).

Chrysanthemum cuttings (T3 pot balls) are planted in plastic pots (diameter 11 cm) using the previously treated soil. The plants are infected with the insects by placing 5 vine weevil larvae (L.2–L.3) per pot into prepared holes. The plants are incubated in the greenhouse at 20° C. and 80% relative atmospheric humidity.

The pots are evaluated after 4 weeks according to the number of dead insects.

The efficacy according to Abbott is 100 if all insects have been killed, it is 0 if the same number of insects is still alive as in the untreated control.

Results

| Granules concentration in ppm | Efficacy according to Abbott |
| --- | --- |
| 1600 | 82 |

Example B2

Test insect: Tenebrio molitor Granules: Granules with Metarhizium anisopliae (obtainable according to Example A)

Experiment

The granules are mixed under the sieved test soil using commercial mixers. Commercial, peat-containing soil is used as substrate. The humidity of the soil is 40% relative humidity. The concentration of the granules in the soil is stated in ppm (mg/l, w/v%).

The sieved soil charged with granules is filled into transparent polystyrene containers (100 ml/container), populated with 10 Tenebrio larvae (d=1.4–1.8 mm) each and closed with a perforated lid. The containers are incubated at 20° C. and 100% relative atmospheric humidity. For each variant, 4 containers with 10 insects each are used.

Evaluation is carried out according to the number of living or dead insects and is stated as efficacy (E) according to Abbott.

The efficacy is 100 if all insects have been killed, it is 0 if the same number of insects is still alive as in the untreated control.

Results

| Granules concentration in ppm | E |
| --- | --- |
| 800 | 100 |
| 400 | 97 |
| 200 | 83 |

We claim:

1. A pesticidal composition comprising granules, microorganisms and an adhesive, wherein said granules consist of semolina particles having a mean diameter of 0.05 to 3.0 mm, said granules contain $2 \times 10^3$ to $2 \times 10^{10}$ spores or conidia of said microorganisms per gram of said granules, said microorganisms are selected from the group consisting of *Metarhizium anisopliae* strain P 0001 deposited under Accession No. DSM 3884 and *Metarhizium anisopliae* strain P 0003 deposited under Accession No. DSM 3885, the adhesive is non-toxic to said microorganisms and is selected from the group consisting of cellulose adhesives, starch adhesives dextran adhesives, alginate adhesives, agar-agar adhesives, gelatin adhesives, gum arabic adhesives, tragacanth adhesives, casein size adhesives, gluten size adhesives, polyvinyl alcohol adhesives, polyvinyl acetate adhesives and mixtures thereof, and said microorganisms and said adhesive are coated on the surface of said granules.

2. The pesticidal composition according to claim 1, further comprising an auxiliary or a pesticidal active compound, wherein said auxiliary is non-toxic to said microorganisms and is selected from the group consisting of antiooxidants, polyalcohols, sugars, lipids, colorants and nutrients, and said pesticidal active compound is non-toxic to said microorganisms.

3. The pesticidal composition according to claim 1, wherein said semolina particles are selected from the group consisting of wheat semolina particles, oat semolina particles, rye semolina particles, corn semolina particles and rice semolina particles.

4. The pesticidal composition according to claim 3, wherein said wheat semolina particles are wheat durum semolina particles.

5. A method of controlling pests, said method comprising applying a pesticidally effective amount of the pesticidal composition according to claim 1 to said pests or their habitat.

6. The method according to claim 5, wherein said pests are selected from the group consisting of arthropods and nematodes.

7. The method according to claim 6, wherein said arthropods are insects.

8. A process for preparing a pesticidal composition according to claim 1, said process comprising:

a) suspending said microorganisms in an aqueous solution comprising said adhesive;

b) mixing the suspension produced in a) with semolina particles having a mean diameter of 0.05 to 3.0 mm so that the surface of said semolina particles is coated with said microorganisms and said adhesive; and c) separating and drying the coated semolina particles produced in b).

9. The process according to claim 8, wherein the aqueous solution in a) further comprises an auxiliary or a pesticidal active compound, wherein said auxiliary is non-toxic to said microorganisms and is selected from the group consisting of antiooxidants, polyalcohols, sugars, lipids, colorants and nutrients, and said pesticidal active compound is non-toxic to said microorganisms.

* * * * *